(12) United States Patent
Hane

(10) Patent No.: US 12,083,275 B2
(45) Date of Patent: Sep. 10, 2024

(54) METHOD OF PRESSURE CONTROL IN A MECHANICAL VENTILATOR WITH NON-PROPORTIONAL SOLENOID VALVES

(71) Applicant: CHINOOK BIOMEDICAL INC., Murillo (CA)

(72) Inventor: Francis Hane, Murillo (CA)

(73) Assignee: Chinook Biomedical Inc., Murillo (CA)

( * ) Notice: Subject to any disclaimer, the term of this patent is extended or adjusted under 35 U.S.C. 154(b) by 537 days.

(21) Appl. No.: 17/347,956

(22) Filed: Jun. 15, 2021

(65) Prior Publication Data

US 2021/0393905 A1    Dec. 23, 2021

Related U.S. Application Data

(60) Provisional application No. 63/042,195, filed on Jun. 22, 2020.

(51) Int. Cl.
*A61M 16/00* (2006.01)
*A61M 16/20* (2006.01)
(52) U.S. Cl.
CPC ...... *A61M 16/024* (2017.08); *A61M 16/0003* (2014.02); *A61M 16/201* (2014.02); *A61M 16/208* (2013.01); *A61M 2016/0027* (2013.01)

(58) Field of Classification Search
CPC .............. A61M 16/024; A61M 16/022; A61M 16/021; A61M 16/026; A61M 16/0003; A61M 16/20; A61M 16/201; A61M 16/202; A61M 16/203; A61M 16/204; A61M 16/205; A61M 16/12; A61M 16/122; A61M 16/125; A61M 16/208; A61M 2016/0015; A61M 2016/0018; A61M 2016/0027; A61M 2016/003; A61M 2016/0033; A61M 2016/0036; A61M 2016/0039; A61M 2016/0042
See application file for complete search history.

(56) References Cited

U.S. PATENT DOCUMENTS

| | | | | |
|---|---|---|---|---|
| 4,414,982 A | * | 11/1983 | Durkan | A61M 16/0051 251/47 |
| 2011/0144514 A1 | * | 6/2011 | Booker | A61M 16/0475 128/207.14 |
| 2014/0007870 A1 | * | 1/2014 | Franberg | A61M 16/206 128/204.23 |
| 2016/0287824 A1 | * | 10/2016 | Chang | A61M 16/0057 |

* cited by examiner

*Primary Examiner* — Joseph D. Boecker
*Assistant Examiner* — Brian T Khong
(74) *Attorney, Agent, or Firm* — Michael R. Williams; Ryan W. Dupuis; Ade & Company Inc.

(57) ABSTRACT

Described herein is a ventilator that is able to use readily available, low cost on/off non-proportional solenoid valves to provide adequate ventilatory control to patients by achieving rapid Airway Pressure while precisely regulating the Airway Pressure.

14 Claims, 3 Drawing Sheets

METHOD OF PRESSURE CONTROL IN A MECHANICAL VENTILATOR WITH NON-PROPORTIONAL SOLENOID VALVES

PRIORITY APPLICATION INFORMATION

The instant application claims the benefit of U.S. Provisional Patent Application Ser. No. 63/042,195, filed Jun. 22, 2020 and entitled "METHOD OF PRESSURE CONTROL IN A MECHANICAL VENTILATOR WITH NON-PROPORTIONAL SOLENOID VALVES", now abandoned, the entire contents of which are incorporated herein by reference for all purposes.

BACKGROUND OF THE INVENTION

A mechanical ventilator is a medical device that is used to provide respiratory support to patients in profound respiratory distress by moving breathable air into and out of the lungs, to deliver breaths to a patient who is physically unable to breath or breathing insufficiently.

Mechanical ventilators known in the art utilize either Pressure Control Mode or Volume Control Mode. In Pressure Control Mode, the ventilator targets a specific Airway Pressure set by the operator. In Volume Control Mode, the ventilator delivers a specified volume of gas. The gas delivered is either air, oxygen, or some ratio of the two.

A mechanical ventilator may either use existing gas supply inputs, typically from a central supply system in a hospital, or generate its own pressurized gas by means of a compressor. A mechanical ventilator must regulate these pressurized gases utilizing solenoid valves to provide the proper gas pressure and volume, at the correct frequency, to provide proper respiratory control to the patient.

The solenoid valves used in mechanical ventilators in the prior art are typically proportional, that is, their output is variable as a function of the pulse width of the input drive signal. This proportionality allows precise control of air delivery as a function of the error signal that is the difference between the desired Airway Pressure (Target Pressure) and measured Airway Pressure. Proportional solenoid valves are considerably more expensive and more difficult to manufacture than non-proportional solenoid valves.

Controlling the pressure in pressure control ventilation requires satisfying two competing interests. First, the gas must be delivered rapidly, reaching the Target Pressure within a very short time, typically 250 ms. Second, the pressure must be accurately metered to maintain precise Airway Pressure, typically within 2 cm H2O of the Target Pressure. Balancing these two requirements is a challenge of considerable difficulty. Fast delivery of air requires valves with large orifices to permit high gas flows while precise pressure regulation requires small orifices to precisely meter small quantities of gas.

Described herein are methods for controlling the Airway Pressure in a mechanical ventilator with simple non-proportional (i.e. on/off) solenoid valves using a pressure chamber to achieve rapid air delivery. Also described are embodiments in which a feedback/machine learning software algorithm is used to predict subsequent gas flow requirements and precisely meter air to regulate Airway Pressure.

SUMMARY OF THE INVENTION

It is therefore an objective of this Invention to provide a ventilator that is able to use readily available, low cost on/off non-proportional solenoid valves to provide adequate ventilatory control to patients by achieving rapid Airway Pressure while precisely regulation the Airway Pressure.

It is therefore another objective of this Invention to provide a ventilator that is of compact size and usable within a hospital setting with a variety of medical air and oxygen gas inputs.

The Invention achieves these objectives by utilizing a pressure accumulator whereby medical air and oxygen is proportioned at the proper ratio and is rapidly delivered to the patient, as discussed herein.

Furthermore, in some embodiments, the Invention utilizes a feedback system to set the pressure of the pressure accumulator to predict the proper quantity of gas to be delivered.

According to a first aspect of the invention, there is provided a method for ventilating a patient comprising:
connecting the patient in need of ventilation at a target pressure to a mechanical ventilator such that breathable air is provided to a patient airway, said mechanical ventilator comprising an apparatus comprising:
a controller;
a pressure accumulator,
at least one medical air inlet for supplying medical air to the pressure accumulator, said at least one medical air inlet comprising a one-way check valve and a non-proportional solenoid;
at least one oxygen inlet for supplying oxygen to the pressure accumulator, said at least one oxygen inlet comprising a one-way check valve and a non-proportional solenoid;
a pressure sensor within the pressure accumulator responsive to the controller for pressurizing the pressure accumulator to a specific pressure prior to start of an inhalation cycle
a gas delivery valve connected to the pressure accumulator for providing air to the patient; and
during a respective one inhalation cycle, said controller measuring inhalation airway pressure of the patient airway over an inhalation cycle time period and calculating rate of pressure change over said inhalation cycle time period; and
during a respective expiration cycle immediately following the respective one inhalation cycle, said controller closing the gas delivery valve and pressurizing the pressure accumulator with medical air and oxygen according to the inhalation airway pressure.

According to another embodiment of the invention, there is provided an apparatus for use with a mechanical ventilator for ventilating a patient at a target pressure, said apparatus comprising:
a controller;
a pressure accumulator,
at least one medical air inlet for supplying medical air to the pressure accumulator, said at least one medical air inlet comprising a one-way check valve and a non-proportional solenoid;
at least one oxygen inlet for supplying oxygen to the pressure accumulator, said at least one oxygen inlet comprising a one-way check valve and a non-proportional solenoid;
a pressure sensor within the pressure accumulator responsive to the controller for pressurizing the pressure accumulator to a specific pressure prior to start of an inhalation cycle
a gas delivery valve connected to the pressure accumulator for providing air to the patient; and said controller being configured such that, during a respective one inhalation cycle, said controller is arranged to measure inhalation airway pressure of the patient airway over an inhalation cycle time period and to calculate rate of pressure change over said inhalation cycle time period; and said controller being arranged, during a respective expiration cycle immediately following the respective one inhalation cycle, to close the gas delivery valve and pressurize the pressure accumulator with medical air and oxygen according to the inhalation airway pressure.

DESCRIPTION OF THE PREFERRED EMBODIMENTS

Figure 1:
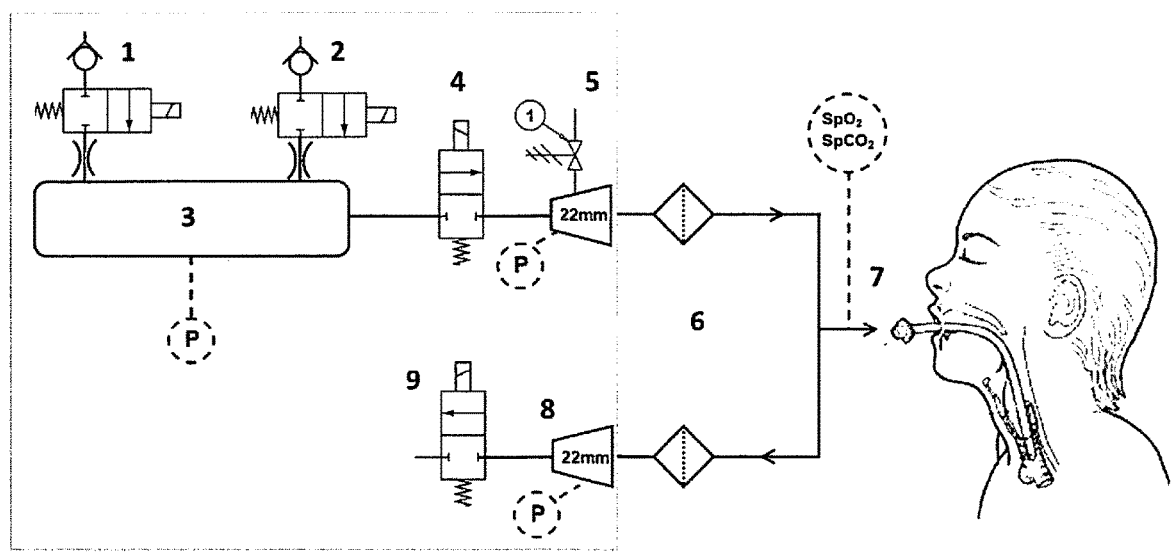
FIG. 1 is a schematic of the gas delivery system of the ventilator. Medical air and oxygen inputs (usually from the hospitals' supply system) pass separately through their respective check valve. Non-proportional solenoid valves are used to charge the pressure accumulator to the proper pressure. A gas delivery valve delivers the pressurized gas from the pressure accumulator to the gas delivery side of the ventilator breathing circuit. An integral expiration valve regulates the Airway Pressure during expiration. A ventilator breathing circuit is connected to the gas delivery and return ports of the ventilator. The ventilator breathing circuit terminates at a "Y" where an endotracheal tube is connected to the ventilator breathing circuit to deliver gas to the patient's lungs.
Figure 2:
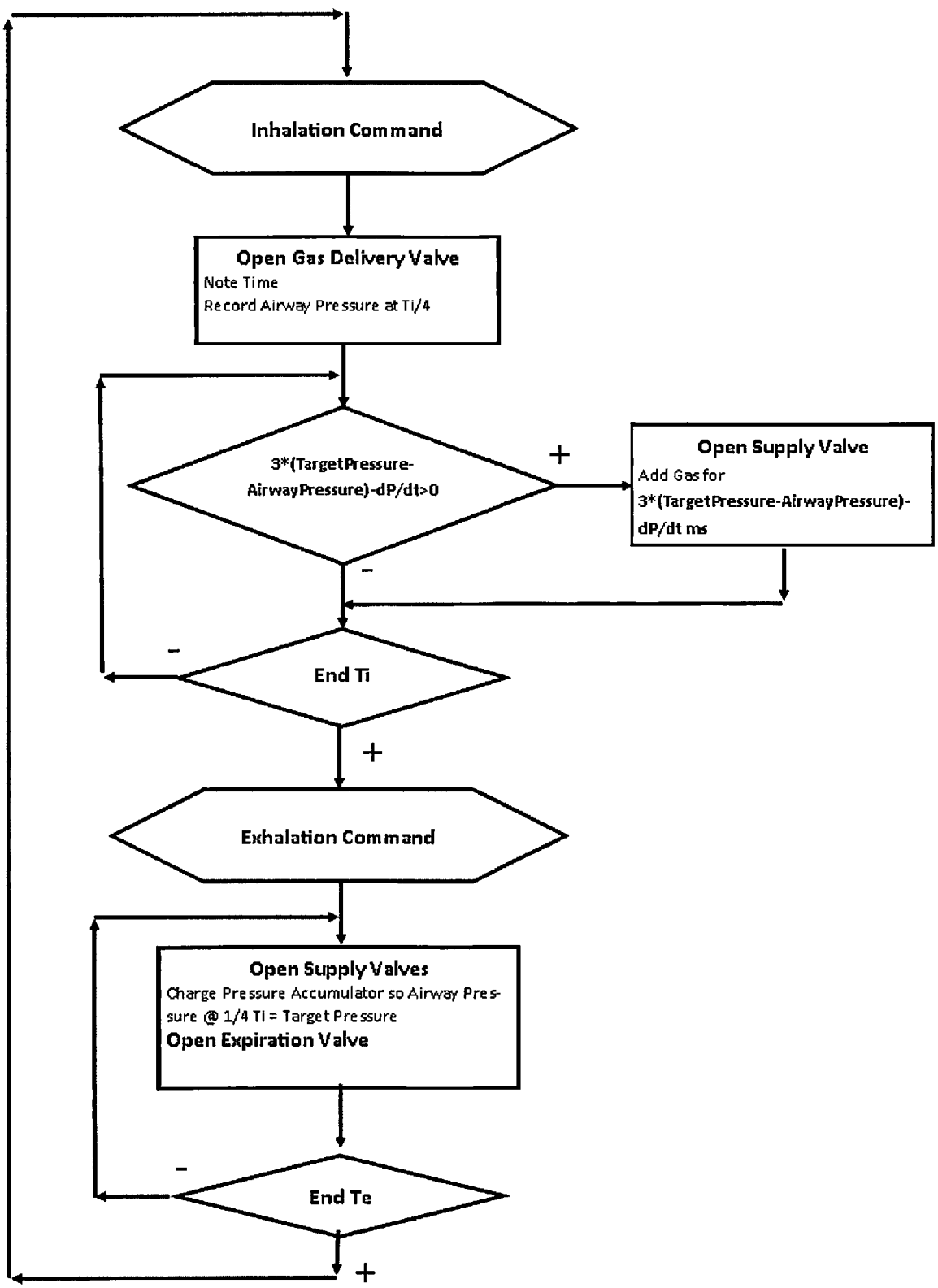
FIG. 2 is a flow chart of the software used to regulate pressure.

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

As used herein, the terms "approximately" and/or "about" refer to a value that is within 10% of the base value. For example, "approximately 10 cm" or "about 10 cm" is to be understood as referring to 9-11 cm.

It is therefore an objective of this Invention to provide a ventilator that is able to use readily available, low cost on/off non-proportional solenoid valves to provide adequate ventilatory control to patients by achieving rapid Airway Pressure while precisely regulation the Airway Pressure.

It is therefore also another objective of this Invention to provide a ventilator that is of compact size and usable within a hospital setting with a variety of medical air and oxygen gas inputs.

The Invention achieves these objectives by utilizing a pressure accumulator whereby medical air and oxygen is proportioned at the proper ratio and is rapidly delivered to the patient.

In one aspect of the invention, there is provided a method for ventilating a patient comprising:

connecting the patient in need of ventilation at a target pressure to a mechanical ventilator such that breathable air is provided to a patient airway, said mechanical ventilator comprising an apparatus comprising:
a controller;
a pressure accumulator,
at least one medical air inlet for supplying medical air to the pressure accumulator, said at least one medical air inlet comprising a one-way check valve and a non-proportional solenoid;
at least one oxygen inlet for supplying oxygen to the pressure accumulator, said at least one oxygen inlet comprising a one-way check valve and a non-proportional solenoid;
a pressure sensor within the pressure accumulator responsive to the controller for pressurizing the pressure accumulator to a specific pressure prior to start of an inhalation cycle
a gas delivery valve connected to the pressure accumulator for providing air to the patient; and
during a respective one inhalation cycle, said controller measuring inhalation airway pressure of the patient airway over an inhalation cycle time period and calculating rate of pressure change over said inhalation cycle time period; and
during a respective expiration cycle immediately following the respective one inhalation cycle, said controller closing the gas delivery valve and pressurizing the pressure accumulator with medical air and oxygen according to the inhalation airway pressure.

As will be apparent, an "inhalation cycle" is when breathable air is supplied from the pressure accumulator via the gas delivery valve to the patient and an "expiration cycle" is when the breathable air or gas exits or returns from the patient for example via a return connection port as known in the art.

Thus, as described herein, the apparatus of the invention can be used in combination with a mechanical ventilator, so as to effectively provide a feedback system which can predict future airway pressure and consequently adjust gas delivery requirements for subsequent breaths. Specifically, as discussed herein, a specially designed pressure accumulator is arranged and/or configured to provide rapid delivery of gas at the required pressure.

As such, this proportional feedback system can be used to regulate the pressure in the pressure accumulator based on the airway pressure for the previous breath. Consequently, in some embodiments, the pressure of any given breath or inhalation cycle is adjusted according to or to reflect or based on the immediately previous breath or inhalation cycle, as discussed herein.

In some embodiments of the invention, the inhalation airway pressure is measured at approximately one fourth of the inhalation cycle time period. That is, if the inhalation time period is for example 1 second, the quarter inhalation airway pressure is measured at 250 ms into that particular inhalation cycle time period.

In some embodiments, a next respective one inhalation cycle's pressure accumulator pressure is calculated from the previous respective one inhalation cycle's pressure accumulator pressure, the target pressure and the previous respective inhalation cycle's quarter inhalation airway pressure.

In some embodiments of the invention, the next respective one inhalation cycle's pressure accumulator pressure is calculated by adding the previous respective one inhalation cycle's pressure accumulator pressure to the difference between the target pressure and the previous respective inhalation cycle's quarter inhalation airway pressure.

In some embodiments of the invention, prior to addition, the difference between the target pressure and the previous respective inhalation cycle's quarter-inhalation airway pressure is modified to account for proportional gain.

In some embodiments of the invention, if the rate of pressure change is greater than zero, applying a pulse of air to the patient airway.

In some embodiments of the invention, the pulse of air is at a pressure that is approximately 3 times the difference between the target pressure and the patient airway pressure minus the rate of pressure change.

As will be appreciated by one of skill in the art, in these embodiments, the controller is in effect a proportional-derivative controller that measures the difference between the Target Pressure and the Airway Pressure and subtracts the rate of pressure change to determine how much metered gas to deliver.

As such, in these embodiments of the invention, the controller predicts the airway pressure at the end of inhalation and delivers a small quantity of gas to maintain the airway pressure at the target pressure during the course of the inhalation cycle and in particular at the end of the inhalation cycle.

That is, in these embodiments, the controller is in effect a proportional-derivative controller to add extra gas should the Airway Pressure fall below the Target Pressure.

In other embodiments of the invention, the controller comprises a machine learning algorithm that analyzes collected data to predict airway pressure and gas delivery requirements for subsequent breaths.

In other embodiments of the invention, the controller measures local minima of airway pressure during at least one respective inhalation cycle and subsequently delivers gas during subsequent breaths at a corresponding time in the subsequent inhalation cycle to just prior to when these measured local minima occurred in the at least one respective inhalation cycle.

According to another aspect of the invention, there is provided an apparatus for use with a mechanical ventilator for ventilating a patient at a target pressure, said apparatus comprising:
  a controller;
  a pressure accumulator,
  at least one medical air inlet for supplying medical air to the pressure accumulator, said at least one medical air inlet comprising a one-way check valve and a non-proportional solenoid;
  at least one oxygen inlet for supplying oxygen to the pressure accumulator, said at least one oxygen inlet comprising a one-way check valve and a non-proportional solenoid;
  a pressure sensor within the pressure accumulator responsive to the controller for pressurizing the pressure accumulator to a specific pressure prior to start of an inhalation cycle
  a gas delivery valve connected to the pressure accumulator for providing air to the patient; and
  said controller being configured such that, during a respective one inhalation cycle, said controller is arranged to measure inhalation airway pressure of the patient airway over an inhalation cycle time period and to calculate rate of pressure change over said inhalation cycle time period; and said controller being arranged, during a respective expiration cycle immediately following the respective one inhalation cycle, to close the gas delivery valve and pressurize the pressure accumulator with medical air and oxygen according to the inhalation airway pressure.

In some embodiments, the inhalation airway pressure is measured at approximately one fourth or one quarter of the inhalation cycle time period.

In some embodiments, the controller is arranged to calculate a next respective one inhalation cycle's pressure accumulator pressure from the previous respective one inhalation cycle's pressure accumulator pressure, the target pressure and the previous respective inhalation cycle's quarter inhalation airway pressure.

In some embodiments, the controller calculates the next respective one inhalation cycle's pressure accumulator pressure by adding the previous respective one inhalation cycle's pressure accumulator pressure to the difference between the target pressure and the previous respective inhalation cycle's quarter inhalation airway pressure.

In some embodiments, prior to addition, the difference between the target pressure and the previous respective inhalation cycle's quarter inhalation airway pressure is modified to account for proportional gain.

In some embodiments, the controller is arranged to apply a pulse of air to the patient airway if the rate of pressure change is greater than zero.

In some embodiments, the pulse of air is at a pressure that is approximately 3 times the difference between the target pressure and the patient airway pressure minus the rate of pressure change.

In some embodiments, the processor is arranged to calculate an estimated end of inhalation airway pressure from the inhalation airway pressure and the rate of pressure change and if the estimated end of inhalation airway pressure is less than the target pressure, the controller is arranged to deliver additional gas so that the inhalation airway pressure does not fall below the target pressure.

With reference to FIG. 1, the pressure accumulator comprises at least two gas inlets (1 & 2), for example, for a medical air inlet and an oxygen inlet. Each of the gas inlets comprise of a 1-way check valve and a solenoid valve. The solenoid valve is preferably a non-proportional solenoid valve, as discussed herein. In some embodiments, the gas inlets (1, 2) comprise an orifice of between about 0.030" and 0.045".

The at least two gas inlets (1, 2) feed a pressure accumulator (3) with a volume of approximately 150 mL. The pressure accumulator has a pressure sensor to provide pressure information to a microcontroller. A gas delivery valve (4) provides air to the patient, for example, via a standard 22 mm patient connection port (5). The patient connection port also has a 1 psi pressure relief valve to protect the patient should the ventilator malfunction and over pressurize the ventilator breathing circuit.

In use, the gas delivery valve (4) forms a ventilator breathing circuit (6) when connected to the patient's endotracheal tube (7). That is, the gas is provided to the ventilator via delivery and return HEPA filters to prevent gas contamination. During exhalation, the gas returns from the patient via a standard 22 mm return patient connection port (8) and expiration valve (9). Filtered expiration gas is vented inside the vented case.

As discussed herein, a mechanical ventilator must accomplish two competing goals: first, it must deliver the proper air pressure within a very short time, typically 250 ms; second, it must regulate the Airway Pressure during the inhalation period.

The first goal, to rapidly deliver air at the proper pressure, is accomplished by pressurizing the pressure accumulator (3) with medical air and oxygen at the selected ratio during the expiration phase when the gas delivery valve is closed. The Invention utilizes a feedback system wherein the pressure at approximately ¼ of the inhalation time is measured. That is, the pressure is measured during the first quarter of the inhalation time period. As will be appreciated by those of skill in the art, this is the latest time that the Airway Pressure should be at the selected pressure during the inhalation cycle. A feedback system adjusts the pressure in the pressure accumulator based on the pressure at ¼ inhalation time of the previous breath. Should the pressure not rise rapidly enough, the subsequent breath will utilize a higher pressure accumulator pressure to deliver the gases more rapidly which may be for example determined via a proportional feedback algorithm.

$$AccumulatorPressure = PreviousAccumulatorPressure + k \cdot (PressureTarget - Pressure@1/4Inspiration$$

Typical proportional gain, k, may be, for example, approximately, 0.5.

Given the lag between the valve opening and a pressure change, predicting when to open the valve for delivering the pulse of air is an important objective of this design goal.

The second goal, to precisely regulate the Airway Pressure is accomplished by a modified proportional-derivative feedback system to calculate when to apply a pulse of air. A Proportional-derivative (PD) feedback system is well known in the prior art. A PD system adjusts an output as a function of the error plus the change in the error, de/dt.

In this Invention, the PD feedback system is modified, so that instead of utilizing the change in error, de/dt, the feedback system utilizes the change in pressure, dP/dt to more accurately predict the Airway Pressure at some future time point in the inhalation cycle.

Figure 4:
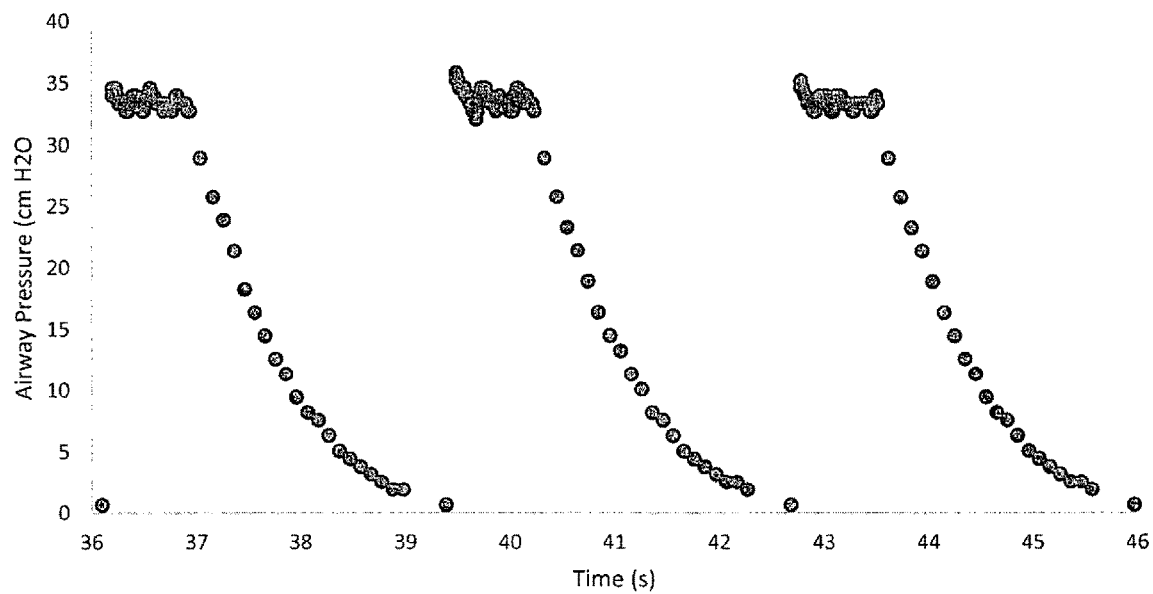
FIG. 4 is a pressure-time graph of the ventilator operating at 35 cm H2O with a lung compliance of 10 mL/mbar and a resistance of 50 cm H2O/L/s.

Once the gas in the pressure accumulator (3) is delivered, the microprocessor monitors the Airway Pressure and calculates the rate of pressure change, dP/dt. If the Pressure Target-Airway Pressure—the rate of pressure change is greater than 0, it is an indication that extra gas will be needed to maintain pressure. This is especially true in lungs with high resistance (FIG. 4) where pressure rises rapidly and once the pressure accumulator has depleted, the pressure falls rapidly as the delivered gas diffuses from the endotracheal tube to the alveoli. In some embodiments, a pulse of air equal to approximately 3 times the difference between the Target Pressure and Airway Pressure minus the rate of pressure change. In some embodiments, an equal amount of time is used as a delay for the gas to diffuse through the restriction. That is, the gas or breathable air is applied in short bursts at higher pressure with a lag between each burst so that the applied gas or breathable air has time to move through the lungs. As will be appreciated by one of skill in the art, this is beneficial for patients with lungs that have a lot of resistance. In this case, the airway pressure is reached prematurely but is the result of air that is in the airway, but has not yet entered the lung. As the air diffuses into the lung, the pressure drops. At this point, another short burst of gas is applied and then shut off, for example, for an equal amount of time as the time of the respective burst or each of the bursts of air, so as to allow the gas to diffuse into the lungs. This can be visualized as for example a "saw tooth" like airway pressure pattern, wherein the air is applied in short bursts over a brief burst time period followed by a closed time period of an approximately similar duration. That is, in some embodiments, the gas or breathable air is applied to a patient with restricted lungs in two or more bursts wherein each burst is separated by a time period approximately the same as the time period of the burst.

$$ExtraGasTime(\text{ms}) = 3 \cdot (TargetPressure - AirwayPressure) - \frac{dP}{dt}$$

Figure 3:
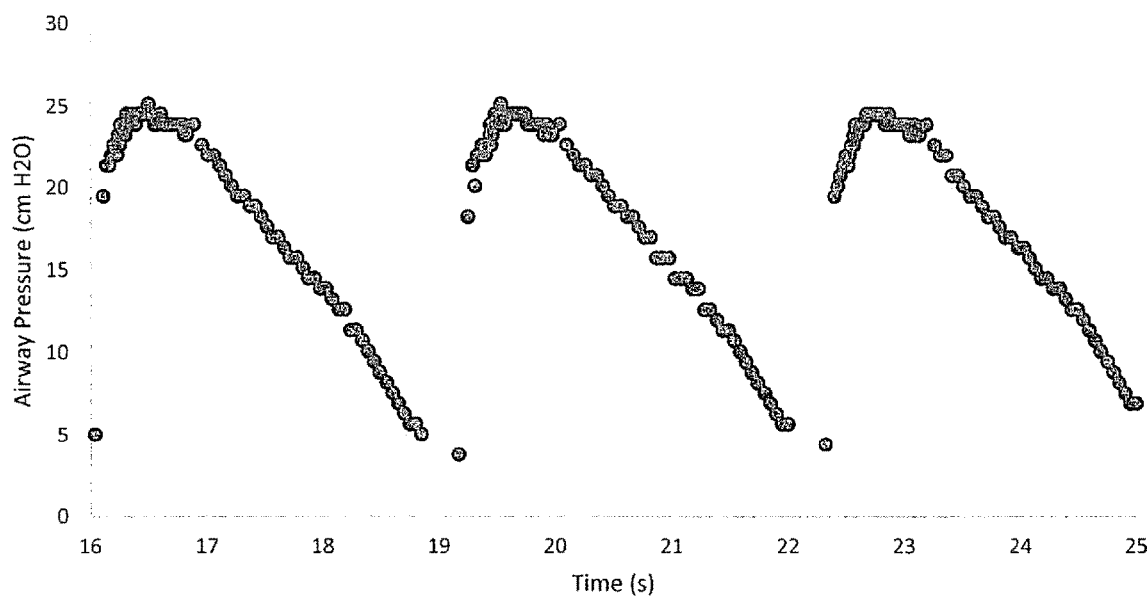
FIG. 3 is a pressure-time graph of the ventilator operating at 25 cm H2O with a lung compliance of 20 mL/mbar and a resistance of 5 cm H2O/L/s.

In lungs with low resistance (FIG. 3), the majority of the gas delivered will come from the pressure accumulator (3) and no extra gas needs to be added. However, in lungs with high resistance (FIG. 4), very little gas comes from the pressure accumulator (3) but small quantities of gas are delivered as the gas diffuses through the restriction. That is, at one time, a small quantity of the gas is applied at one time and then allowed to diffuse into the lungs before the next small quantity or burst is applied. In effect, in these embodiments, the inhalation cycle comprises two or more short bursts of air, each burst of air separated by a gap or lag period during which no air is applied. In some embodiments, the duration of each burst and each corresponding lag may be approximately the same.

In these embodiments, the Pressure Accumulator (3) will be charged to a low-pressure value so that any gas delivery to maintain Airway Pressure results in a very small pressure change, for example, typically 2 cm H2O.

In another embodiment of the Invention, the microprocessor uses the Airway Pressure and pressure change to estimate the Airway Pressure at the end of inhalation. If the Airway Pressure is predicted to fall below the Target Pressure, additional gas is delivered prior to the Airway Pressure falling below the Target Pressure.

In another embodiment of the Invention, the microprocessor will record local pressure minima during inhalation, for example, the time point within the inhalation cycle time period during at least one inhalation cycle wherein the minima occurred and the controller will deliver extra gas at the corresponding time point in subsequent inhalation cycles, that is, in subsequent breaths prior to the known drop in Airway Pressure. In some embodiments, the microprocessor or processor or controller utilizes a machine learning (also known as an artificial intelligence) algorithm, known in the prior art, to carry out a multivariate analysis of this data to look for commonalities that can be used to predict future gas delivery requirements and time the gas delivery to maintain pressure.

While the preferred embodiments of the invention have been described above, it will be recognized and understood that various modifications may be made therein, and the appended claims are intended to cover all such modifications which may fall within the spirit and scope of the invention.

The invention claimed is:
1. A method for ventilating a patient comprising:
connecting the patient in need of ventilation at a target pressure to a mechanical ventilator such that a breathable air comprising medical air and/or oxygen, is provided to a patient airway, said mechanical ventilator comprising an apparatus comprising:

a controller comprising a processor;
a pressure accumulator,
at least one medical air inlet for supplying the medical air to the pressure accumulator, said at least one medical air inlet comprising a one-way check valve and a non-proportional solenoid valve;
at least one oxygen inlet for supplying the oxygen to the pressure accumulator, said at least one oxygen inlet comprising a one-way check valve and a non-proportional solenoid valve;
a pressure sensor within the pressure accumulator responsive to the controller for pressurizing the pressure accumulator to an accumulator pressure prior to start of an inhalation cycle;
a gas delivery valve connected to the pressure accumulator for providing the breathable air to the patient; and
during a respective one inhalation cycle, said controller measuring an inhalation airway pressure of the patient airway over an inhalation cycle time period and calculating rate of pressure change over said inhalation cycle time period; and
during a respective expiration cycle immediately following the respective one inhalation cycle, said controller closing the gas delivery valve and pressurizing the pressure accumulator with the breathable air according to the inhalation airway pressure,
wherein the processor calculates an estimated end of inhalation airway pressure from the inhalation airway pressure and the rate of pressure change and if the estimated end of inhalation airway pressure is less than the target pressure, additional breathable air is delivered so that the inhalation airway pressure does not fall below the target pressure.

2. The method according to claim 1 wherein the inhalation airway pressure is measured at approximately one fourth of the inhalation cycle time period.

3. The method according to claim 2 wherein a next respective one inhalation cycle's pressure accumulator pressure is calculated from the previous respective one inhalation cycle's pressure accumulator pressure, the target pressure and the previous respective inhalation cycle's quarter inhalation airway pressure.

4. The method according to claim 3 wherein the next respective one inhalation cycle's pressure accumulator pressure is calculated by adding the previous respective one inhalation cycle's pressure accumulator pressure to the difference between the target pressure and the previous respective inhalation cycle's quarter inhalation airway pressure.

5. The method according to claim 4 wherein prior to addition, the difference between the target pressure and the previous respective inhalation cycle's quarter inhalation airway pressure is modified to account for proportional gain.

6. The method according to claim 2 wherein if the rate of pressure change is greater than zero, applying a pulse of the breathable air to the patient airway.

7. The method according to claim 6 wherein the pulse of the breathable air is at a pressure that is approximately 3 times the difference between the target pressure and the patient airway pressure minus the rate of pressure change.

8. An apparatus for use with a mechanical ventilator for ventilating a patient at a target pressure, said apparatus comprising:
a controller comprising a processor;
a pressure accumulator,
at least one medical air inlet for supplying medical air to the pressure accumulator, said at least one medical air inlet comprising a one-way check valve and a non-proportional solenoid valve;
at least one oxygen inlet for supplying oxygen to the pressure accumulator, said at least one oxygen inlet comprising a one-way check valve and a non-proportional solenoid valve;
a pressure sensor within the pressure accumulator responsive to the controller for pressurizing the pressure accumulator to an accumulator pressure prior to start of an inhalation cycle
a gas delivery valve connected to the pressure accumulator for providing the medical air and/or the oxygen to the patient; and
said controller being configured such that, during a respective one inhalation cycle, said controller measures an inhalation airway pressure of the patient airway over an inhalation cycle time period and to calculates rate of pressure change over said inhalation cycle time period; and
said controller being configured, during a respective expiration cycle immediately following the respective one inhalation cycle, to close the gas delivery valve and pressurize the pressure accumulator with the medical air and/or the oxygen according to the inhalation airway pressure,
wherein the processor is arranged to calculate an estimated end of inhalation airway pressure from the inhalation airway pressure and the rate of pressure change and if the estimated end of inhalation airway pressure is less than the target pressure, the controller is arranged to deliver additional medical air and/or oxygen so that the inhalation airway pressure does not fall below the target pressure.

9. The apparatus according to claim 8 wherein the inhalation airway pressure is measured at approximately one fourth of the inhalation cycle time period.

10. The apparatus according to claim 9 wherein the controller is arranged to calculate a next respective one inhalation cycle's pressure accumulator pressure from the previous respective one inhalation cycle's pressure accumulator pressure, the target pressure and the previous respective inhalation cycle's quarter inhalation airway pressure.

11. The apparatus according to claim 10 wherein the controller calculates the next respective one inhalation cycle's pressure accumulator pressure by adding the previous respective one inhalation cycle's pressure accumulator pressure to the difference between the target pressure and the previous respective inhalation cycle's quarter inhalation airway pressure.

12. The apparatus according to claim 11 wherein prior to addition, the difference between the target pressure and the previous respective inhalation cycle's quarter inhalation airway pressure is modified to account for proportional gain, that is, the rate of increase of airway pressure.

13. The apparatus according to claim 9 wherein the controller is arranged to apply a pulse of the medical air and/or the oxygen to the patient airway if the rate of pressure change is greater than zero.

14. The apparatus according to claim 13 wherein the pulse of the medical air and/or the oxygen is at a pressure that is approximately 3 times the difference between the target pressure and the patient airway pressure minus the rate of pressure change.

* * * * *